United States Patent [19]

Shirafuji et al.

[11] Patent Number: 5,231,194
[45] Date of Patent: Jul. 27, 1993

[54] PROCESS FOR PRODUCING COUMARIN DERIVATIVES

[75] Inventors: Tamio Shirafuji; Kiyomi Sakai; Kensen Okusako, all of Ehime, Japan

[73] Assignee: Sumitomo Chemical Co., Ltd., Osaka, Japan

[21] Appl. No.: 631,316

[22] Filed: Dec. 21, 1990

[30] Foreign Application Priority Data

Dec. 21, 1989 [JP] Japan .................................. 1-333153
Jul. 24, 1990 [JP] Japan .................................. 2-197098

[51] Int. Cl.$^5$ .......................................... C07D 311/20
[52] U.S. Cl. .................................................. 549/290
[58] Field of Search ........................................ 549/290

[56] References Cited

U.S. PATENT DOCUMENTS

| | | | |
|---|---|---|---|
| 2,542,965 | 2/1951 | Levesque | 549/290 |
| 3,442,910 | 5/1969 | Thweatt | 549/290 |
| 3,925,422 | 12/1975 | Schaafsma et al. | 549/290 |
| 3,936,473 | 2/1976 | Symon et al. | 549/290 |
| 4,772,728 | 9/1988 | Korte et al. | 549/290 |

FOREIGN PATENT DOCUMENTS

| | | | |
|---|---|---|---|
| 0420532 | 4/1991 | European Pat. Off. | 549/290 |
| 60-181082 | 9/1985 | Japan . | |
| 0682457 | 11/1952 | United Kingdom . | |
| 0683344 | 11/1952 | United Kingdom . | |

OTHER PUBLICATIONS

"Preparation and catalytic hydrogenation of 4,6-dimethyl-and 4,7-dimethyl-8-methoxycoumarins. A 4-methyldihydrocoumarin synthesis", Chemical Abstracts, vol. 95, No. 5, Aug. 3, 1981, p. 733.

"Catalytic synthesis of coumarin derivatives of beta-arrylamino ketones", Chemical Abstracts, vol. 70 No. 5, Feb. 3, 1969, p. 1974.

"Study of the heterogeneous catalytic acylation of phenols in the manufacture of coumarin and chromone" Chemical Abstracts, vol. 108, No. 17, Apr. 25, 1988, p. 723.

Primary Examiner—C. Warren Ivy
Assistant Examiner—A. A. Owens
Attorney, Agent, or Firm—Sughrue, Mion, Zinn, Macpeak & Seas

[57] ABSTRACT

A process for producing a coumarin derivative represented by formula (II):

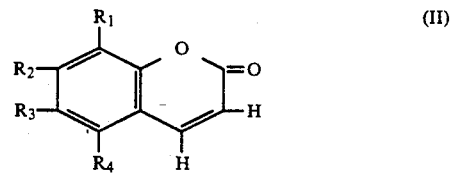

wherein $R_1$ to $R_4$ are as defined in the specification, comprising the step of: subjecting to a ring formation and dehydrogenation reaction a 3-(2-cyclohexanoyl)-propionic acid ester derivative represented by formula (I):

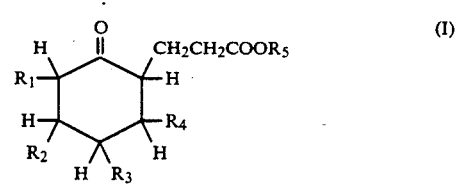

wherein $R_1$ to $R_4$ are as defined in the specification, the ring formation and dehydrogenation reaction being (1) conducted by use of a catalyst comprising a carrier having supported thereon palladium and either of chromium oxide and chromium hydroxide, or (2) conducted by use of a catalyst comprising a carrier having supported thereon palladium or a catalyst comprising a carrier having supported thereon palladium and either of chromium oxide and chromium hydroxide, in the presence of a promoter which is at least one member selected from the group consisting of magnesium trisilicate, zirconia, metallic chromium, and metallic tungsten.

13 Claims, No Drawings

PROCESS FOR PRODUCING COUMARIN DERIVATIVES

FIELD OF THE INVENTION

The present invention relates to a process for producing a coumarin derivative from a 3-(2-cyclohexanoyl)-propionic acid ester derivative.

Coumarin derivatives, along with dihydrocoumarin derivatives formed as by-products, are important compounds particularly in the perfume industry and also as intermediates for agricultural chemicals, medicines, and dyes.

BACKGROUND OF THE INVENTION

Conventionally known methods for producing coumarin derivatives include, for example, a process in which a hydrogenation-dehydrogenation catalyst, such as palladium, etc., and a 3-(2-cyclohexanoyl)propionic acid ester derivative as a starting material are first introduced into a reactor at a time, and ring formation and dehydrogenation reaction is then conducted with heating, as described in U.S. Pat. No. 3,442,910, and a process in which the ring formation and dehydrogenation reaction for producing a coumarin derivative is performed in the co-presence of a noble metal catalyst, such as palladium, etc., and a promoter such as barium sulfate, nickel oxide, etc., as described, e.g., in JP-A-60-181082. The term "JP-A" as used herein means an "unexamined published Japanese patent application".

However, the conventional processes cannot always produce coumarin derivatives in high yields.

SUMMARY OF THE INVENTION

The present inventors have conducted intensive studies in order to develop a process for producing coumarin derivatives in good yields at low cost. As a result, a novel catalyst and promoter for use in the ring formation and dehydrogenation reaction for producing a coumarin derivative have been found. The present invention has been completed based on this finding.

It is, therefore, an object of the present invention to provide a process for producing a coumarin derivative in a high yield.

Other objects and effects of the present invention will be apparent from the following description.

The present invention provides a process for producing a coumarin derivative represented by formula (II):

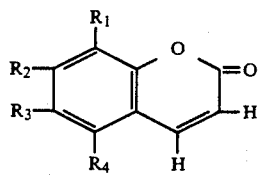

wherein $R_1$ to $R_4$ each represents a hydrogen atom, a methyl group, or an ethyl group, provided that at least two of $R_1$ to $R_4$ each represents a hydrogen atom, the process comprising the step of: subjecting to a ring formation and dehydrogenation reaction a 3-(2-cyclohexanoyl)propionic acid ester derivative represented by formula (I):

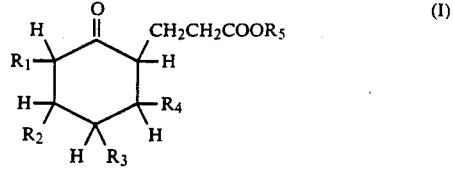

wherein $R_1$ to $R_4$ are as defined above, and $R_5$ represents an alkyl group having 1 to 4 carbon atoms, the ring formation and dehydrogenation reaction being (1) conducted by use of a catalyst comprising a carrier having supported thereon palladium and either of chromium oxide and chromium hydroxide, or (2) conducted by use of a catalyst comprising a carrier having supported thereon palladium or a catalyst comprising a carrier having supported thereon palladium and either of chromium oxide and chromium hydroxide, in the presence of a promoter which is at least one member selected from the group consisting of magnesium trisilicate, zirconia, metallic chromium, and metallic tungsten.

DETAILED DESCRIPTION OF THE INVENTION

The 3-(2-cyclohexanoyl)propionic acid ester derivative used in the present invention is represented by formula (I) given above. Examples of this compound include methyl 3-(2-cyclohexanoyl)propionate, ethyl 3-(2-cyclohexanoyl)propionate, butyl 3-(2-cyclohexanoyl)propionate, methyl 3-(2-cyclohexanoyl-3-methyl)propionate, methyl 3-(2-cyclohexanoyl-5-methyl)propionate, propyl 3-(2-cyclohexanoyl-4-ethyl)-propionate, propyl 3-(2-cyclohexanoyl-3,4-diethyl)propionate, propyl 3-(2-cyclohexanoyl-3,4-dimethyl)propionate, methyl 3-(2-cyclohexanoyl-3,5-diethyl)propionate, methyl 3-(2-cyclohexanoyl-3-ethyl-6-methyl)propionate, and the like, but the compound of formula (I) is not limited to these examples.

The catalyst used in the present invention is a heterogeneous metal catalyst which comprises palladium supported on a carrier, or comprises palladium and either of chromium oxide and chromium hydroxide all of which are supported on a carrier. The carrier preferably is at least one member selected from the group consisting of compounds of Group IIA, IIIA, and IVA elements of the periodic table, such as carbon, alumina, silica gel, barium sulfate, and the others.

These catalysts may be prepared by known methods, for example, by the impregnation-fixation technique as described, e.g., in Shokubai Jikken Manual (Catalyst Experiment Manual), edited by Shokubai Gakkai, published by Maki Shoten, Japan, in which a carrier is impregnated with a metal compound and the resulting carrier is subjected to hydrogen reduction at a high temperature. However, a commercially available catalyst may also be used as it is.

The amount of the catalyst used for the ring formation and dehydrogenation reaction is generally about from 0.1 to 5% by weight, preferably about from 0.3 to 2% by weight, based on the amount of the 3-(2-cyclohexanoyl)propionic acid ester derivative, since too small an amount of the catalyst results in very low reactivity, whereas too large an amount thereof results not only in an increased amount of by-products because of too high reactivity, but also in an increased cost.

In the case of using the catalyst comprising palladium and either of chromium oxide and chromium hydroxide all of which are supported on a carrier, the amount of the chromium oxide or chromium hydroxide is generally about from 1 to 20% by weight, preferably about from 5 to 15% by weight, based on the amount of the palladium.

Along with the palladium-based catalyst described above, at least one of magnesium trisilicate, zirconia, metallic chromium, and metallic tungsten may be used as a promoter for practicing the ring formation and dehydrogenation reaction. As this promoter, a commercially available promoter may be used as it is without any treatment.

The amount of the promoter used is generally about from 0.01 to 3% by weight, preferably about from 0.05 to 2% by weight, based on the amount of the 3-(2-cyclohexanoyl)propionic acid ester derivative.

The ring formation and dehydrogenation reaction of the 3-(2-cyclohexanoyl)propionic acid ester derivative may be conducted generally at about from 100° to 350° C., preferably at about from 230° to 280° C. Temperatures outside the above range are not preferred because too low a temperature results in low reactivity, while a temperature exceeding about 350° C. tends to cause the starting material and/or the product to decompose.

A solvent may be used in performing the ring formation and dehydrogenation reaction. Examples of the solvent include phenyl ether, benzyl ether, methyl α-naphthyl ether, ethylnaphthalene, dimethylbiphenyl, dodecane, tetradecane, tetralin, acetophenone, phenyl propyl ketone, methyl benzoate, dimethyl glutamate, and the like. The amount of the solvent is generally from about 0.5 to about 10 times, preferably from about 1 to about 7 times, the amount of the 3-(2-cyclohexanoly)propionic acid derivative.

The ring formation and dehydrogenation reaction can be carried out by introducing the 3-(2-cyclohexanoyl)propionic acid ester derivative and either the catalyst or both the catalyst and the promoter, and then heating the resulting mixture, along with a solvent if required, at a predetermined temperature generally for about 5 hours to about 50 hours. The reaction is generally carried out in an inert gas atmosphere under ordinary pressure. As a result, 3,4-dihydrocoumarin derivative is obtained in a yield of about from 30 to 45%, and coumarin derivative is obtained in a yield of about from 30 to 40%. Besides these compounds, o-ethylphenols, methyl dihydrocinnamic acid esters, octahydrocoumarins, etc. result as by-products.

According to the process of the present invention, coumarin derivatives can be produced in higher yields as compared with conventional processes.

The present invention will be explained in more detail by reference to the following examples, which should not be construed to be limiting the scope of the invention. Unless otherwise indicated, all parts, percents, etc. are by weight.

EXAMPLE 1

In a four-necked flask, 200 g of methyl 3-(2-cyclohexanoyl)propionate was mixed with 2.0 g of a catalyst consisting of active carbon and 5% by weight of palladium supported thereon and with 0.2 g of magnesium trisilicate as a promoter. The resulting mixture in the flask was heated at 240° C. for 10 hours with stirring at 300 rpm in a nitrogen atmosphere. Thereafter, the mixture was heated to 260° C. and maintained at this temperature for 5 hours, and was then heated to 270° C. and maintained at this temperature for 15 hours.

After completion of the reaction, the resulting reaction mixture was filtered to remove the catalyst and promoter, and then analyzed by gas chromatography. As a result, it was found that the conversion of the methyl 3-(2-cyclohexanoyl)propionate was 99.8% and the yields of coumarin and 3,4-dihydrocoumarin based on the methyl 3-(2-cyclohexanoyl)propionate were 28.7% and 36.6%, respectively.

EXAMPLE 2

In a four-necked flask, 300 g of methyl 3-(2-cyclohexanoyl)propionate was mixed with 3.0 g of a catalyst consisting of active carbon and 5% by weight of palladium supported thereon and with 0.3 g of zirconia as a promoter. The resulting mixture in the flask was heated at 240° C. for 10 hours with stirring at 300 rpm in a nitrogen atmosphere. Thereafter, the mixture was heated to 260° C. and maintained at this temperature for 5 hours, and was then heated to 270° C. and maintained at this temperature for 15 hours.

Analysis of the resulting reaction mixture by gas chromatography revealed that the conversion of the methyl 3-(2-cyclohexanoyl)propionate was 99.7% and the yields of coumarin and 3,4-dihydrocoumarin based on the methyl 3-(2-cyclohexanoyl)propionate were 28.0% and 40.6%, respectively.

EXAMPLE 3

The same procedures as in Example 2 were repeated except that the catalyst of Example 2 was replaced by 3.0 g of a catalyst consisting of active carbon and 5% by weight of palladium and 0.5% by weight of chromium hydroxide both supported on the active carbon, and the promoter was not used.

Analysis of the resulting reaction mixture by gas chromatography revealed that the conversion of the methyl 3-(2-cyclohexanoyl)propionate was 99.5% and the yields of coumarin and 3,4-dihydrocoumarin based on the methyl 3-(2-cyclohexanoyl)propionate were 28.7% and 42.1%, respectively.

EXAMPLE 4

The same procedures as in Example 2 were repeated except that the catalyst of Example 2 was replaced by 3.0 g of a catalyst consisting of active carbon and 5% by weight of palladium and 0.5% by weight of chromium hydroxide both supported on the active carbon, and the promoter was replaced by 0.3 g of a fine powder of metallic chromium and 0.6 g of zirconia.

Analysis of the resulting reaction mixture by gas chromatography revealed that the conversion of the methyl 3-(2-cyclohexanoyl)propionate was 99.9% and the yields of coumarin and 3,4-dihydrocoumarin based on the methyl 3-(2-cyclohexanoyl)propionate were 33.9% and 40.9%, respectively.

EXAMPLE 5

In a four-necked flask, 300 g of methyl 3-(2-cyclohexanoyl)propionate was mixed with 3.0 g of a catalyst consisting of active carbon and 5% by weight of palladium supported thereon and with 0.3 g of a fine powder of metallic chromium as a promoter. The resulting mixture in the flask was heated at 240° C. for 10 hours with stirring at 300 rpm in a nitrogen atmosphere. Thereafter, the mixture was heated to 255° C. and maintained at this temperature for 1 hour, and was then heated to 270° C. and maintained at this temperature for 15 hours.

Analysis of the resulting reaction mixture by gas chromatography revealed that the conversion of the methyl 3-(2-cyclohexanoyl)propionate was 99.4% and the yields of coumarin and 3,4-dihydrocoumarin based on the methyl 3-(2-cyclohexanoyl)propionate were 29.2% and 40.3%, respectively.

EXAMPLE 6

The same procedures as in Example 2 were repeated except that the promoter of Example 2 was replaced by 0.3 g of a fine powder of metallic chromium and 0.6 g of zirconia.

Analysis of the resulting reaction mixture by gas chromatography revealed that the conversion of the methyl 3-(2-cyclohexanoyl)propionate was 99.7% and the yields of coumarin and 3,4-dihydrocoumarin based on the methyl 3-(2-cyclohexanoyl)propionate were 30.3% and 35.6%, respectively.

EXAMPLE 7

The same procedures as in Example 2 were repeated except that the promoter of Example 2 was replaced by 0.3 g of a fine powder of metallic tungsten.

Analysis of the resulting reaction mixture by gas chromatography revealed that the conversion of the methyl 3-(2-cyclohexanoyl)propionate was 99.6% and the yields of coumarin and 3,4-dihydrocoumarin based on the methyl 3-(2-cyclohexanoyl)propionate were 32.3% and 27.6%, respectively.

COMPARATIVE EXAMPLE 1

The same procedures as in Example 2 were repeated except that the 0.3 g of zirconia was not used.

Analysis of the resulting reaction mixture by gas chromatography revealed that the conversion of the methyl 3-(2-cyclohexanoyl)propionate was 99.7% and the yields of coumarin and 3,4-dihydrocoumarin based on the methyl 3-(2-cyclohexanoyl)propionate were 19.2% and 47.2%, respectively.

COMPARATIVE EXAMPLE 2

The same procedures as in Example 2 were repeated except that the promoter of Example 2 was replaced by 0.3 g of barium sulfate.

Analysis of the resulting reaction mixture by gas chromatography revealed that the conversion of the methyl 3-(2-cyclohexanoyl)propionate was 99.6% and the yields of coumarin and 3,4-dihydrocoumarin based on the methyl 3-(2-cyclohexanoyl)propionate were 28.0% and 37.3%, respectively.

COMPARATIVE EXAMPLE 3

The same procedures as in Example 2 were repeated except that the promoter of Example 2 was replaced by 0.3 g of a fine powder of metallic molybdenum.

Analysis of the resulting reaction mixture by gas chromatography revealed that the conversion of the methyl 3-(2-cyclohexanoyl)propionate was 99.0% and the yields of coumarin and 3,4-dihydrocoumarin based on the methyl 3-(2-cyclohexanoyl)propionate were 21.2% and 29.2%, respectively.

COMPARATIVE EXAMPLE 4

The same procedures as in Example 2 were repeated except that the promoter of Example 2 was replaced by 0.3 g of tungsten trioxide.

Analysis of the resulting reaction mixture by gas chromatography revealed that the conversion of the methyl 3-(2-cyclohexanoyl)propionate was 99.2% and the yields of coumarin and 3,4-dihydrocoumarin based on the methyl 3-(2-cyclohexanoyl)propionate were 23.1% and 38.4%, respectively.

While the invention has been described in detail and with reference to specific embodiments thereof, it will be apparent to one skilled in the art that various changes and modifications can be made therein without departing from the spirit and scope thereof.

What is claimed is:

1. A process for producing a coumarin derivative represented by formula (II):

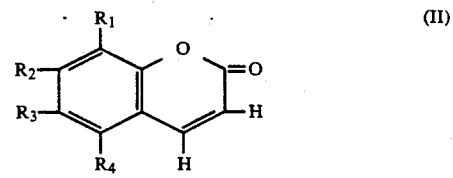

wherein $R_1$ to $R_4$ each represents a hydrogen atom, a methyl group, or an ethyl group, provided that at least two of $R_1$ to $R_4$ each represents a hydrogen atom, said process comprising the step of: subjecting to a ring formation and dehydrogenation reaction a 3-(2-cyclohexanoyl)propionic acid ester derivative represented by formula (I):

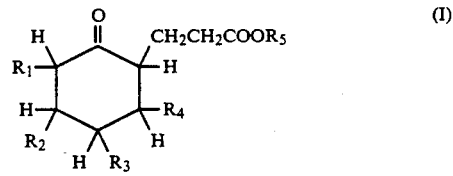

wherein $R_1$ to $R_4$ are as defined above, and $R_5$ represents an alkyl group having 1 to 4 carbon atoms, said ring formation and dehydrogenation reaction being conducted by use of a catalyst comprising a carrier having supported thereon palladium and either of chromium oxide and chromium hydroxide in which a coumarin derivative and 3,4-dihydrocoumarin derivative are obtained in yields of from 30 to 40% and 30 to 45%, respectively.

2. A process for producing a coumarin derivative represented by formula (II):

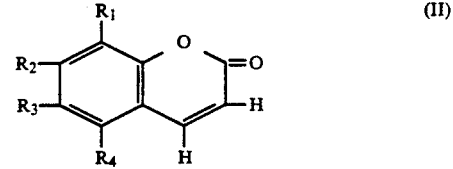

wherein $R_1$ to $R_4$ each represents a hydrogen atom, a methyl group, or an ethyl group, provided that at least two of $R_1$ to $R_4$ each represents a hydrogen atom, said process comprising the step of: subjecting to a ring formation and dehydrogenation reaction a 3-(2-cyclohexanoyl)propionic acid ester derivative represented by formula (I):

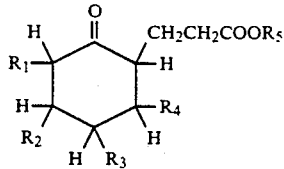

wherein $R_1$ to $R_4$ are as defined above, and $R_5$ represents an alkyl group having 1 to 4 carbon atoms, said ring formation and dehydrogenation reaction being conducted by use of a catalyst comprising a carrier having supported thereon palladium or a catalyst comprising a carrier having supported thereon palladium and either of chromium oxide and chromium hydroxide, in the presence of a promoter which is at least one member selected from the group consisting of metallic chromium, and metallic tungsten in which a coumarin derivative and a 3,4-dihydrocoumarin derivative are obtained in yields of from 30 to 40% and 30 to 45%, respectively.

3. A process as claimed in claim 1, wherein said 3-(2-cyclohexanoyl)propionic acid ester derivative is methyl 3-(2-cyclohexanoyl)propionate.

4. A process as claimed in claim 2, wherein said 3-(2-cyclohexanoyl)propionic acid ester derivative is methyl 3-(2-cyclohexanoyl)propionate.

5. A process as claimed in claim 1, wherein said carrier is at least one member selected from the group consisting of carbon, alumina, silica gel, and barium sulfate.

6. A process as claimed in claim 2, wherein said carrier is at least one member selected from the group consisting of carbon, alumina, silica gel, and barium sulfate.

7. A process as claimed in claim 1, wherein the amount of said chromium oxide or chromium hydroxide supported on the carrier is about from 1 to 20 wt % based on the amount of said palladium.

8. A process as claimed in claim 2, wherein the amount of said chromium oxide or chromium hydroxide supported on the carrier is about from 1 to 20 wt % based on the amount of said palladium.

9. A process as claimed in claim 1, wherein said catalyst is used in an amount of about from 0.1 to 5 wt % based on the amount of said 3-(2-cyclohexanoyl)propionic acid ester derivative.

10. A process as claimed in claim 2, wherein said catalyst is used in an amount of about from 0.1 to 5 wt % based on the amount of said 3-(2-cyclohexanoyl)propionic acid ester derivative.

11. A process as claimed in claim 2, wherein said promoter is used in an amount of about from 0.01 to 3 wt % based on the amount of said 3-(2-cyclohexanoyl)propionic acid ester derivative.

12. A process as claimed in claim 1, wherein said ring formation and dehydrogenation reaction is conducted at a temperature of about from 100° to 350° C.

13. A process as claimed in claim 2, wherein said ring formation and dehydrogenation reaction is conducted at a temperature of about from 100° to 350° C.

* * * * *